(12) United States Patent
Schmidt

(10) Patent No.: US 11,498,891 B2
(45) Date of Patent: Nov. 15, 2022

(54) CATALYSTS, PREPARATION METHOD THEREOF, AND SELECTIVE HYDROGENATION PROCESSES

(71) Applicant: W.R. GRACE & CO.-CONN, Columbia, MD (US)

(72) Inventor: Stephen R. Schmidt, Silver Spring, MD (US)

(73) Assignee: W.R. Grace & Co.-Conn, Columbia, MD (US)

( * ) Notice: Subject to any disclaimer, the term of this patent is extended or adjusted under 35 U.S.C. 154(b) by 1 day.

(21) Appl. No.: 17/263,279

(22) PCT Filed: Aug. 6, 2019

(86) PCT No.: PCT/US2019/045228
§ 371 (c)(1),
(2) Date: Jan. 26, 2021

(87) PCT Pub. No.: WO2020/033358
PCT Pub. Date: Feb. 13, 2020

(65) Prior Publication Data
US 2021/0284591 A1    Sep. 16, 2021

Related U.S. Application Data

(60) Provisional application No. 62/715,926, filed on Aug. 8, 2018.

(51) Int. Cl.
| | | |
|---|---|---|
| *C07C 29/17* | (2006.01) | |
| *B01J 8/02* | (2006.01) | |
| *B01J 21/02* | (2006.01) | |
| *B01J 35/02* | (2006.01) | |
| *B01J 37/00* | (2006.01) | |
| *B01J 37/04* | (2006.01) | |
| *B01J 37/08* | (2006.01) | |

(52) U.S. Cl.
CPC ............. *C07C 29/172* (2013.01); *B01J 8/025* (2013.01); *B01J 21/02* (2013.01); *B01J 35/023* (2013.01); *B01J 37/009* (2013.01); *B01J 37/0063* (2013.01); *B01J 37/04* (2013.01); *B01J 37/08* (2013.01)

(58) Field of Classification Search
CPC .......... B01J 35/023; B01J 23/10; B01J 21/02; C07C 29/172; C07C 31/207; C07C 29/17
See application file for complete search history.

(56) References Cited

U.S. PATENT DOCUMENTS

| | | | |
|---|---|---|---|
| 6,262,317 B1 * | 7/2001 | Becker | ................... B01J 8/0278 568/861 |
| 6,395,934 B1 | 5/2002 | Wegener et al. | |
| 7,553,517 B1 | 6/2009 | Jablonski et al. | |
| 2005/0209350 A1 | 9/2005 | Espinoza et al. | |
| 2010/0016643 A1 | 1/2010 | Pinkos et al. | |
| 2013/0172578 A1 | 7/2013 | Allgeier et al. | |
| 2014/0349844 A1 | 11/2014 | Liang et al. | |

FOREIGN PATENT DOCUMENTS

| | | |
|---|---|---|
| CN | 201210212109.2 A | 7/2011 |
| CN | 106861704 A | 6/2017 |
| WO | WO-2008/071090 A1 | 6/2008 |
| WO | 2018/060269 A1 | 4/2018 |
| WO | 2018/098053 A2 | 5/2018 |

OTHER PUBLICATIONS

Zhao et al (CN 106861701 A machine translation published Jun. 20, 2017).*
Extended European Search Report on EP Application No. 19847556.8 dated Jun. 3, 2022 (8 pages).
Wen, G., et al., "Preparation of Ce-modified Raney Ni Catalysts and Their Application in Aqueous-Phase Reforming of Cellulose," Catalysis Letters, 141(2):1851-1858 (2011) (8 pages).

* cited by examiner

*Primary Examiner* — Jafar F Parsa
(74) *Attorney, Agent, or Firm* — Foley & Lardner LLP

(57) ABSTRACT

The present invention relates to a process for making 1,4-butanediol. The process may include reacting a solution comprising 1,4-butynediol with hydrogen in a presence of a catalyst. The catalyst may include cerium.

12 Claims, No Drawings

CATALYSTS, PREPARATION METHOD THEREOF, AND SELECTIVE HYDROGENATION PROCESSES

CROSS REFERENCE TO RELATED APPLICATIONS

This application claims the benefit of the filing date of U.S. Provisional Patent Application No. 62/715,926 filed Aug. 8, 2018, entitled "CATALYSTS, PREPARATION METHOD THEREOF, AND SELECTIVE HYDROGENATION PROCESSES", the disclosure of which is hereby incorporated by reference.

FIELD OF THE INVENTION

The present invention relates to catalysts, and more particularly, to the catalysts for preparing 1,4 butanediol, a preparation method thereof, and a selective hydrogenation process employing the catalysts.

BACKGROUND

Skeletal metal nickel in granular fixed bed form is generally used industrially to make butanediol (BDO), a component in making polyesters, from the unsaturated compound 1,4 butynediol (BYD).

U.S. Pat. No. 6,262,317 discloses a process for preparing 1,4-butanediol by continuous catalytic hydrogenation of 1,4-butynediol. The process comprises reacting 1,4-butynediol with hydrogen in the liquid continuous phase in the presence of a heterogeneous hydrogenation catalyst. The catalyst generally comprises one or more elements of transition groups I, VI, VII and VIII of the Periodic Table of the Elements. The catalyst preferably further comprises at least one element selected from the elements of main groups II, III, IV and VI, transition groups II, III, IV and V of the Periodic Table of the Elements, and the lanthanides as a promoter to increase the activity. The promoter content of the catalyst is generally up to 5% by weight. The catalysts may be precipitation, supported, or skeletal type catalysts.

CN 201210212109.2 discloses a preparation and an activation method of a skeletal metal nickel-aluminum-X catalyst specially for hydrogenation preparation of 1,4-butanediol from 1,4-butynediol. X represents Mg, B, Sr, Cr, S, Ti, La, Sn, W, Mo or Fe.

The current catalysts typically have a predictable limited lifetime. The current process produces n-butanol and other byproducts at a gradually increasing rate until a maximum specification limit is reached, which defines the end of useful life of the bed's catalyst. The acidic Al species present in a skeletal metal catalyst such as hydrous alumina residues from a leaching process are considered as one main cause in producing the byproducts including butanol. Skeletal metal catalysts may in general contain small amounts of added elements as promoters, whose functions include improvement of activity, selectivity and stability of the catalyst in the chemical environment of a given hydrogenation process. Some promoters for skeletal metals such as the conventional Mo, Cr, or Fe may actually increase formation of butanol byproduct due to the increasing surface acidity. Operating conditions such as relatively low temperature, relatively high pressure, and control of feed pH have been optimized previously and their combination still fails to suppress butanol formation adequately. There is a desire in developing a process for making butanediol while formation of n-butanol and other byproducts is minimized and/or delayed. Butanediol is a main component in making polyesters.

Because downstream usages have impurity limits on the butanediol, reducing contaminants in the butanediol during the process for making the butanediol can significantly reduce cost, for example, associated with separation (e.g. distillation) of the impurity from the butanediol later.

BRIEF SUMMARY

The present invention provides a process for making 1,4-butanediol from a 1,4-butynediol solution in a present of a catalyst, which includes cerium. The process for making 1,4-butanediol unexpectedly generates a significantly lower amount of a main byproduct, butanol.

Accordingly, one example of the present invention is a process for making 1,4-butanediol. The process may include reacting a solution comprising 1,4-butynediol with hydrogen in a presence of a catalyst, which includes cerium as a promoter.

Another example of the present invention is a catalyst for making 1,4-butanediol. The catalyst may be a skeletal metal catalyst, which includes cerium as a promoter.

Another example of the present invention is a process of preparing a catalyst. The process may include melting and mixing cerium oxide, a first element, and a second element to form an alloy, followed by activation using an alkali solution to form the catalyst. The first element may be Ni and the second element may be aluminum.

DETAILED DESCRIPTION

The present invention is described with reference to embodiments of the invention in order to provide a better understanding by those skilled in the art of the technical solutions of the present disclosure.

A number modified by "about" herein means that the number can vary by 10% thereof. A numerical range modified by "about" herein means that the upper and lower limits of the numerical range can vary by 10% thereof.

One example of the present invention is a process for making 1,4-butanediol. The process may include reacting a solution which includes 1,4-butynediol with hydrogen in a presence of a catalyst, which includes cerium as a promoter.

The solution which includes 1,4-butynediol may be a technical-grade 1,4-butynediol which is in an form of an aqueous solution and can additionally contain, as insoluble or dissolved constituents, components from the butynediol synthesis, e.g. copper, bismuth, aluminum or silicon compounds. The main solvent for the solution which includes 1,4-butynediol is usually water. The solution which includes 1,4-butynediol may also comprise other solvents such as methanol, ethanol, propanol, butanol or 1,4-butanediol. The 1,4-butynediol content in the solution is generally from 10 to 90% by weight, preferably from 20 to 80% by weight, particularly preferably from 30 to 70% by weight of the solution. In one embodiment, the solution which includes 1,4-butynediol is 100% pure butynediol.

The solution which includes 1,4-butynediol may have a pH in a range from about 6.0 to about 11.0, preferably about 9 to about 10.

The hydrogen required for the reaction is preferably used in pure form. But it can also contain further components such as methane and carbon monoxide. The hydrogen pressure applied to a fixed bed reactor for this process may be in a range from about 15 to about 30 MPa. The inlet temperature of the fixed bed reactor may be in a range from about 80° C. to about 120° C. The flow rate of the feed solution may be chosen by those skilled in the art to allow for a desired level of conversion of the butynediol. The desired level of conversion of the butynediol in turn depends on whether the process stream is partly recycled to the reactor inlet. For non-recycled process streams, the desired conversion level in a 'single pass' is usually very high, i.e. over 99 wt % on organic compounds basis.

According to the present invention, the catalysts used are those which are capable of hydrogenating C≡C triple and double bonds to single bonds. The catalyst may be in a form of a fixed-bed, a slurry or suspension, or a combination thereof. In one embodiment, the catalyst is in the form of the fixed-bed, and may have a particle size in a range of about 1 mm to about 8 mm, preferably about 2 mm to about 5 mm. In another embodiment, the catalyst is in the form of the slurry or suspension, and may have a median particle size in a range of about 10 μm to about 100 μm, preferably about 20 μm to about 80 μm.

The catalyst may further include at least a first element selected from the group consisting of Ni, Co, Cu, Fe, and mixtures thereof. In one embodiment, the first element is Ni. The catalyst may further include at least a second element selected from the group consisting of aluminum, molybdenum, chromium, iron, copper, tin, zirconium, zinc, titanium, vanadium, and mixtures thereof. In one embodiment, the second element is aluminum.

The catalyst may be a skeletal metal catalyst. Suitable skeletal metal catalysts include skeletal metal nickel, skeletal metal copper, skeletal metal cobalt, skeletal metal nickel/molybdenum, skeletal metal nickel/copper, skeletal metal nickel/chromium, skeletal metal nickel/chromium/iron or rhenium sponge.

Cerium may be present in the catalyst in an amount ranging from about 1% to about 5%, preferably about 1.5% to about 3.0% by weight of the catalyst.

The molar ratio of hydrogen to butynediol in the reactor is at least 3:1, preferably from 4:1 to 100:1.

When a fixed-bed reactor is used in the process of the present invention, the space velocities of the solution and gas flowing through the fixed-bed of the catalyst are not limited. One of ordinary skill in the art can adjust the space velocities of the solution and gas to obtain optimum yield of 1,4-butanediol with a low amount of by products such as butanol.

The catalyst according to the present invention may comprise only one type of the catalyst or a mixture of several types of catalysts. The mixture of several types of catalysts can be present as pseudohomogeneous mixture or as a structured bed in which individual reaction zones each are composed of a pseudohomogenous catalyst bed.

It is also possible to combine the methods, for example, to use one catalyst type at the beginning of the reaction and to use a mixture further downstream.

The process may produce butanol as a byproduct in a range of less than about 3.0% by weight, preferably less than about 2.5% by weight based on a total weight of the butanol and the 1,4-butanediol.

In one embodiment of the process for making 1,4-butanediol, the catalyst is a skeletal element catalyst. The catalyst includes at least a first element selected from the group consisting of Ni, Co, Cu, Fe, and mixtures thereof, at least a second element selected from the group consisting of aluminum, molybdenum, chromium, iron, copper, tin, zirconium, zinc, titanium, vanadium, and mixtures thereof, and cerium. The cerium is present in an amount ranging from about 1% to about 5% by weight of the catalyst. The solution comprising 1,4-butynediol has a pH of about 9.0 to about 10.0. The process produces butanol as a byproduct in a range of less than about 3.0% by weight based on a total weight of the butanol and the 1,4-butanediol.

Another example of the present invention is a catalyst for making 1,4-butanediol. The catalyst may include a skeletal metal catalyst, which includes cerium as a promoter. Cerium is present in the catalyst in an amount ranging from about 1.0% to about 5.0% by weight, preferably about 1.5% to about 3.0% by weight of the catalyst. In one embodiment comprising about 1.0% to about 5.0% by weight of cerium, the first element of the skeletal metal is nickel and the second element of the skeletal metal is aluminum.

Another example of the present invention is a process of preparing a catalyst. The process may include melting and mixing cerium oxide, a first element, and a second element to form an alloy. Then, the alloy is activated by contacting with an alkali solution. In one embodiment, the alkali solution is an aqueous solution of sodium hydroxide or potassium hydroxide having a concentration in a range of 1% to 25% by weight.

The first element may be selected from the group consisting of Ni, Co, Cu, Fe, and mixtures thereof. The second element may be selected from the group consisting of aluminum, molybdenum, chromium, iron, copper, tin, zirconium, zinc, titanium, vanadium, and mixtures thereof. In one embodiment, the first element is Ni and the second element is aluminum. Ni may be present in an amount ranging from about 40% to about 60% by weight based on a total weight of the cerium oxide, Ni, and aluminum. Aluminum may be present in an amount ranging from about 40% to about 60% by weight based on a total weight of the cerium oxide, Ni, and aluminum. Cerium oxide may be present in an amount ranging from about 1% to about 5% by weight, preferably from about 1.5% to about 3.5% by weight, based on a total weight of the cerium oxide, Ni, and aluminum. The cerium oxide may be converted into cerium in the alloy during the melting and mixing process.

In one embodiment, the alkali solution is pumped continuously through the alloy bed to activate the alloy. In another embodiment, the alloy particles are added into the alkali solution in batches to activate the alloy. In one embodiment, the catalyst is a skeletal metal catalyst.

In one embodiment, the process of preparing a catalyst includes melting and mixing cerium oxide, a first element, and a second element to form an alloy and contacting the alloy with an alkali aqueous solution to produce the catalyst. The first element is selected from the group consisting of Ni, Co, Cu, Fe, and mixtures thereof, and the second element is selected from the group consisting of aluminum, molybdenum, chromium, iron, copper, tin, zirconium, zinc, titanium, vanadium, and mixtures thereof. Cerium oxide is present in an amount ranging from about 1% to about 5% by weight based on a total weight of the cerium oxide, the first element, and the second element. In one embodiment comprising about 1.0% to about 5.0% by weight of cerium, the first element of the skeletal metal is nickel and the second element of the skeletal metal is aluminum.

Another example of the present invention is the catalyst produced by the process of preparing the catalyst according to one embodiment of the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Hereinafter, the present invention will be described in more detail with reference to Examples. However, the scope of the present invention is not limited to the following Examples.

EXAMPLES

Comparative Example 1: Un-Promoted Nickel Catalyst Catalyst Preparation

An alloy containing 58% by weight of Al and 42% by weight of Ni was formed by melting and mixing the two components. The alloy was then crushed and sieved into alloy particles in a range of 8-12 mesh size or having diameters in a range of about 2 mm to about 3 mm.

A 390 g portion of the alloy particles was placed in a beaker to form a "bed." This bed of alloy particles was converted to catalysts by contacting with a 'leachant,' which includes pumping five portions of aqueous NaOH solutions continuously through the alloy bed at a constant rate. Each portion of the aqueous NaOH solutions is 18 liters, and the strength of the five portions was increasing during the process from 0.9%, then 1.75%, 2.6%, 3.5% and finally 4.35% respectively. Each portion of aqueous NaOH solution was delivered through the alloy bed in 40 minutes while an immersed cooling coil (with internal water flow) is used to control the temperature of the process at a target of 38° C.

The catalysts were then washed with 2 liters of a 0.25% NaOH solution for 10 minutes, then with water at 45° C. until the effluent washing water reached a pH of 9.

Catalytic Testing

The prepared catalysts were maintained in water-wetted state as they were loaded into a vertical column reactor with bed dimensions having an inner diameter of about 0.5 inches and a height of about 6 inches. This amounts to a catalyst bed having a volume of 18 mL.

Reactant feed solution was prepared by dissolving solid 2-butyne-1,4 diol at 35% by weight in water. As a variable to be tested for impact on selectivity, the pH of the reactant feed solution was adjusted to be either 5.0 or 10.0 by addition of small amounts of 15% NaOH solution.

Reaction conditions employed were: inlet temperature of 100° C., peak temperature: 150° C. (outlet temperature), hydrogen pressure=2500 psig (17 MPa), and a controllable range of liquid feed flow rate: 0.25-0.35 mL/min. Co-current upward flow of $H_2$ gas (300 mL/min) and the liquid was maintained.

During the course of testing this catalyst charge, the liquid feed flow rate was increased at various times and then maintained at a constant level for several days. Feed source was switched between pH 10 and 5 as another independent variable. The pH of the reactant feed solution employed and sequence of the liquid flow rates are listed in Table 1.

Product assays, stated in wt. % of organic products, were determined by GC analysis, using a Restek Stabilwax 30×0.32×0.5 column, ethanol solvent at 90%, diglyme as internal standard, and flame ionization detector. Reported yields for each condition in Table 1 are averages from samples taken after each 8 hours of continuous operation.

The main byproduct of interest, n-butanol ("BuOH") ranged from 3.1% to 3.8% over the various conditions for this standard baseline catalyst. The butanol yield is lower when a higher pH of the feed solution is used. A second by-product, hydroxybutoxy tetrahydrofuran, the cyclized acetal formed by reaction of product and feed molecules and dehydration, is listed as 'acetal' in Table 1. Unconverted butynediol is referred to as 'BYD' and % conversion is based on the BYD residual level subtracted from 100%.

Comparative Example 2: La-Promoted Nickel Catalyst

The procedures of Comparative Example 1 were followed with respect to catalyst preparation including alloy formation and activation, catalyst testing, and analysis of catalyzed products in the BYD-BDO system. The alloy preparation used a mixture of 58% Al, 2% Ni, and 40% of a 6% La-94% Ni binary alloy by weight (American Elements). Bulk chemical analysis of the resulting three-component alloy by ICP yielded 2.6% La by weight. By similar analysis, the activated catalysts contained 2.9% La by weight.

The catalyst testing at each combination of BYD feed pH and liquid flow rates yielded significantly higher range of butanol, that is, 5.8-6.2% by weight, as shown in Table 1.

Example 1: Ce-Promoted Nickel Catalyst

The procedures of Comparative Example 1 were followed with respect to catalyst preparation including alloy formation and activation, catalyst testing, and analysis of catalyzed products in the BYD-BDO system. Compared to Comparative Example 1, the alloy preparation in Example 1 differed from the standard Ni-Al type by use of cerium oxide, $CeO_2$, in granular form (0.5-1.0 mm diameter) added into the alloyed mixture at 1.6% by weight along with 57.8% Al by weight and 40.6% Ni by weight. The mixing and melting process converted the $CeO_2$ to Ce, which was incorporated into the element alloy. X-ray diffraction on the resulting solid alloy indicated absence of $CeO_2$ starting material. Bulk chemical analysis of the alloy by ICP yielded 1.3% Ce by weight. By similar analysis, the activated catalysts contained 1.5% Ce by weight after selective removal of Al.

Application of the catalysts with BYD feed solution at pH 10 yielded a significantly lower range of butanol, that is, 2.5%-3.2% by weight depending on the flow rates, as shown in Table 1.

Example 2: Ce-Promoted Nickel Catalyst (Higher Ce Content)

The procedures of Comparative Example 1 were followed with respect to catalyst preparation including alloy formation and activation, catalyst testing, and analysis of catalyzed products in the BYD-BDO system. The alloy preparation followed the method of Example 1, but with cerium oxide added into the alloyed mixture at 3.0% by weight along with 57.7% Al by weight and 39.3% Ni by weight. Bulk chemical analysis of the alloy by ICP yielded 1.9% Ce by weight. By similar analysis, the activated catalyst contained 2.9% Ce by weight.

Application of the catalysts at various combinations of BYD feed solution at pH 10 and varied flow rates yielded a further lower range of butanol, that is, 2.1% -2.8% by weight, as shown Table 1.

Effect of pH of the BYD Feed Solution was Studied as Below:

Three consecutive stages of testing were performed with the above catalyst still charged to the fixed bed reactor. In the three consecutive stages, pH of the BYD feed solution varied at respectively 8, 9, and 11. Each stage was of about 5 days duration at fixed feed flow rate of 0.30 cc/minute. The BDO yields and byproduct contents are shown in Table 1. As shown in Example 2 of Table 1, the butanol byproduct continues to decrease as pH of the BYD feed solution is raised.

However, the acetal byproduct increases at pH 11 (to 1.2%), continuing a trend seen at pH 10 (0.7%). The total content of the combined butanol and acetal byproducts is lowest at the pH 9-10 range.

Example 3: Ce-Promoted Nickel Catalyst

The procedures of Example 2 were followed with respect to the alloy preparation including alloy formation and activation, catalyst testing, and analysis of catalyzed products in the BYD-BDO system. Bulk chemical analysis of the activated catalysts showed that the catalyst contained 2.1% Ce.

Application of the catalysts with feed solution at pH 10 and the relatively high flow rate of 0.4 mL/min, similar as in Comparative Example 2 using La promoter, yielded a butanol content of 3.4% by weight, as shown Table 1.

These examples demonstrate the utility of cerium promoter to unexpectedly improve the selectivity of the process by significantly reducing formation of butanol byproduct.

technical features or the equivalent features of the technical features without departing from the inventive concept. For example, technical scheme may be obtained by replacing the features described above as disclosed in this disclosure (but not limited to) with similar features.

The invention claimed is:

1. A process for making 1,4-butanediol, the process comprising: reacting a solution comprising 1,4-butynediol with hydrogen in a presence of a catalyst;
    wherein:
        the catalyst comprises cerium; and
        the catalyst is a skeletal catalyst comprising at least a first element selected from the group consisting of Ni, Co, Cu, Fe, and mixtures thereof and at least a second element selected from the group consisting of aluminum, molybdenum, chromium, iron, copper, tin, zirconium, zinc, titanium, vanadium, and mixtures thereof.

2. The process of claim 1, wherein the catalyst is in a form of a fixed-bed, a suspension, or a combination thereof.

3. The process of claim 1, wherein the catalyst is in the form of the fixed-bed, and has a particle size in a range of about 1 mm to about 8 mm.

4. The process of claim 1, wherein the catalyst is in the form of the suspension, and has a median particle size in a range of about 10 to about 100 μm.

5. The process of claim 1, wherein the first element is Ni.

6. The process of claim 1, wherein the second element is aluminum.

7. The process of claim 1, wherein the catalyst is a skeletal metal catalyst.

8. The process of claim 1, wherein cerium is present in an amount ranging from about 1% to about 5% by weight of the catalyst.

TABLE 1

| Example | Catalyst | | Catalytic Test Conditions | | Time (hrs) on stream | | | Product Yields % | | |
|---|---|---|---|---|---|---|---|---|---|---|
| | % Ni | % Promoter | Feed Rate (mL/min.) | Feed pH | At this pH, flow | Cumulative | Conversion* | BDO | BuOH | Acetal |
| Comparative 1 | 51.9 | 0 | 0.25 | 10 | 96 | 96 | 99.5 | 95.6 | 3.3 | 0.25 |
| | | | 0.30 | 10 | 120 | 216 | 99.6 | 95.4 | 3.1 | 0.8 |
| | | | 0.30 | 5 | 104 | 320 | 99.8 | 95.2 | 3.8 | 0.27 |
| Example 1 | 50.4 | 1.5 Ce | 0.25 | 10 | 220 | 220 | 99.8 | 96.6 | 2.5 | 0.44 |
| Example 2 | 50.7 | 2.9 Ce | 0.25 | 10 | 104 | 104 | 99.5 | 96.1 | 2.4 | 0.41 |
| Example 2 | 50.7 | 2.9 Ce | 0.25 | 10 | 76 | 180 | 99.8 | 96.5 | 2.8 | 0.09 |
| Example 2 | 50.7 | 2.9 Ce | 0.30 | 5 | 116 | 296 | 99.8 | 95.2 | 4.1 | 0.10 |
| Example 2 | 50.7 | 2.9 Ce | 0.30 | 8 | 96 | 496 | 99.9 | 96.3 | 3.4 | 0.02 |
| Example 2 | 50.7 | 2.9 Ce | 0.30 | 9 | 96 | 592 | 99.7 | 96.9 | 2.6 | 0.06 |
| Example 2 | 50.7 | 2.9 Ce | 0.30 | 10 | 104 | 400 | 99.8 | 96.9 | 2.1 | 0.73 |
| Example 2 | 50.7 | 2.9 Ce | 0.30 | 11 | 87 | 679 | 99.4 | 96.4 | 1.8 | 1.2 |
| Comparative 2 | 50.3 | 2.6 La | 0.40 | 10 | 35 | 35 | 99.6 | 85.7 | 5.6 | NA |
| | 50.3 | 2.6 La | 0.40 | 5 | 14 | 49 | 99.8 | 80.5 | 5.9 | NA |
| Example 3 | 54.7 | 2.1 Ce | 0.40 | 10 | 91 | 91 | 99.4 | 95.5 | 3.4 | 0.6 |

The principle and the embodiment of the disclosures are set forth in the specification. The description of the embodiments of the present disclosure is only used to help understand the method of the present disclosure and the core idea thereof. Meanwhile, for a person of ordinary skill in the art, the disclosure relates to the scope of the disclosure, and the technical scheme is not limited to the specific combination of the technical features, and also should covered other technical schemes which are formed by combining the 9. The process of claim 1, wherein cerium is present in an amount ranging from about 1.5% to about 3.0% by weight of the catalyst.

10. The process of claim 1, wherein the solution comprising 1,4-butynediol has a pH in a range from about 6.0 to about 11.0.

11. The process of claim 1, wherein the solution comprising 1,4-butynediol has a pH of about 9.0 to about 10.0.

12. The process of claim 1, wherein the process produces butanol as a byproduct in a range of less than about 3.0% by weight based on a total weight of the butanol and the 1,4-butanediol.

\* \* \* \* \*